United States Patent
Dath et al.

(10) Patent No.: US 6,858,133 B2
(45) Date of Patent: Feb. 22, 2005

(54) PRODUCTION OF OLEFINS (75) Inventors: Jean-Pierre Dath, Beloeil (BE);
Walter Vermeiren, Houthalen (BE);
Koen Herrebout, Houston, TX (US)

(73) Assignee: Atofina Research S.A., Feluy (BE)

( * ) Notice: Subject to any disclaimer, the term of this patent is extended or adjusted under 35 U.S.C. 154(b) by 272 days.

(21) Appl. No.: 10/127,930

(22) Filed: Apr. 23, 2002

(65) Prior Publication Data
US 2003/0062291 A1 Apr. 3, 2003

Related U.S. Application Data (62) Division of application No. 09/596,406, filed on Jun. 19, 2000.

(30) Foreign Application Priority Data

Jun. 17, 1999 (BE) .......................................... 99111725

(51) Int. Cl.[7] ............................................. C10G 29/16
(52) U.S. Cl. ........................ 208/245; 208/248; 208/213
(58) Field of Search ................................ 208/245, 248, 208/213

(56) References Cited

FOREIGN PATENT DOCUMENTS

| EP | 0034444 | * | 8/1981 |
| EP | 0109060 | * | 5/1984 |

* cited by examiner

*Primary Examiner*—Thuan Dinh Dang
(74) *Attorney, Agent, or Firm*—William D. Jackson (57) ABSTRACT

A process for desulfurising an olefin-containing hydrocarbon feedstock including sulfur-containing hydrocarbon compounds as impurities, the process comprising passing a hydrocarbon feedstock containing one or more olefins through a reactor containing a crystalline silicate selected from the group consisting of an MFI-type crystalline silicate having a silicon/aluminum atomic ratio of at least 180 and an MEL-type crystalline silicate having a silicon/aluminum atomic ratio of from 150 to 800 which has been subjected to a steaming step to produce an effluent with an olefin content of lower molecular weight than that of the feedstock and removing hydrogen sulphide from the effluent.

12 Claims, 2 Drawing Sheets

FIG. 1

PRODUCTION OF OLEFINS

This application is a division of pending prior application Ser. No. 09/596,406, filed Jun. 19, 2000.

BACKGROUND TO THE INVENTION

The present invention relates to a process for cracking an olefin-rich hydrocarbon feedstock which is selective towards light olefins in the effluent. In particular, olefinic feedstocks from refineries or petrochemical plants can be converted selectively so as to redistribute the olefin content of the feedstock in the resultant effluent. The present invention further relates to a process for desulphurising such a feedstock which includes sulphur-containing hydrocarbon compounds as impurities.

DESCRIPTION OF THE PRIOR ART

It is known in the art to use zeolites to convert long chain paraffins into lighter products, for example in the catalytic dewaxing of petroleum feedstocks. While it is not the objective of dewaxing, at least parts of the paraffinic hydrocarbons are converted into olefins. It is known in such processes to use crystalline silicates for example of the MFI or MEL type, the three-letter designations "MFI" and "MEL" each representing a particular crystalline silicate structure type as established by the Structure Commission of the International Zeolite Association. Examples of a crystalline silicate of the MFI type are the synthetic zeolite ZSM-5 and silicalite and other MFI type crystalline silicates are known in the art. An example of a crystalline silicate of the MEL type is the synthetic zeolite ZSM-11.

GB-A-1323710 discloses a dewaxing process for the removal of straight-chain paraffins and slightly branched-chain paraffins, from hydrocarbon feedstocks utilising a crystalline silicate catalyst, in particular ZSM-5. US-A-4247388 also discloses a method of catalytic hydrodewaxing of petroleum and synthetic hydrocarbon feedstocks using a crystalline silicate of the ZSM-5 type. Similar dewaxing processes are disclosed in U.S. Pat. No. 4,284,529 and U.S. Pat. No. 5,614,079. The catalysts are crystalline aluminosilicates and the above-identified prior art documents disclose the use of a wide range of Si/Al ratios and differing reaction conditions for the disclosed dewaxing processes.

GB-A-2185753 discloses the dewaxing of hydrocarbon feedstocks using a silicalite catalyst. U.S. Pat. No. 4,394,251 discloses hydrocarbon conversion with a crystalline silicate particle having an aluminium-containing outer shell.

It is also known in the art to effect selective conversion of hydrocarbon feeds containing straight-chain and/or slightly branched-chain hydrocarbons, in particular paraffins, into a lower molecular weight product mixture containing a significant amount of olefins. The conversion is effected by contacting the feed with a crystalline silicate known as silicalite, as disclosed in GB-A-2075045, U.S. Pat. No. 4,401,555 and U.S. Pat. No. 4,309,276. Silicalite is disclosed in U.S. Pat. No. 4,061,724.

Silicalite catalysts exist having varying silicon/aluminium atomic ratios and different crystalline forms. EP-A-0146524 and 0146525 in the name of Cosden Technology, Inc. disclose crystalline silicas of the silicalite type having monoclinic symmetry and a process for their preparation. These silicates have a silicon to aluminium atomic ratio of greater than 80.

WO-A-97/04871 discloses the treatment of a medium pore zeolite with steam followed by treatment with an acidic solution for improving the butene selectivity of the zeolite in catalytic cracking.

A paper entitled "De-alumination of HZSM-5 zeolites: Effect of steaming on acidity and aromatization activity", de Lucas et al, Applied Catalysis A: General 154 1997 221–240, published by Elsevier Science B. V. discloses the conversion of acetone/n-butanol mixtures to hydrocarbons over such dealuminated zeolites.

It is yet further known, for example from U.S. Pat. No. 4,171,257, to dewax petroleum distillates using a crystalline silicate catalyst such as ZSM-5 to produce a light olefin fraction, for example a $C_3$ to $C_4$ olefin fraction. Typically, the reactor temperature reaches around 500°C and the reactor employs a low hydrocarbon partial pressure which favours the conversion of the petroleum distillates into propylene. Dewaxing cracks paraffinic chains leading to a decrease in the viscosity of the feedstock distillates, but also yields a minor production of olefins from the cracked paraffins.

EP-A-0305720 discloses the production of gaseous olefins by catalytic conversion of hydrocarbons. EP-B-0347003 discloses a process for the conversion of a hydrocarbonaceous feedstock into light olefins. WO-A-90/11338 discloses a process for the conversion of $C_2$–$C_{12}$ paraffinic hydrocarbons to petrochemical feedstocks, in particular to $C_2$ to $C_4$ olefins. U.S. Pat. No. 5,043,522 and EP-A-0395345 disclose the production of olefins from paraffins having four or more carbon atoms. EP-A-0511013 discloses the production of olefins from hydrocarbons using a steam activated catalyst containing phosphorous and H-ZSM-5. U.S. Pat. No. 4,810,356 discloses a process for the treatment of gas oils by dewaxing over a silicalite catalyst. GB-A-2156845 discloses the production of isobutylene from propylene or a mixture of hydrocarbons containing propylene. GB-A-2159833 discloses the production of a isobutylene by the catalytic cracking of light distillates.

It is known in the art that for the crystalline silicates exemplified above, long chain olefins tend to crack at a much higher rate than the corresponding long chain paraffins.

It is further known that when crystalline silicates are employed as catalysts for the conversion of paraffins into olefins, such conversion is not stable against time. The conversion rate decreases as the time on stream increases, which is due to formation of coke (carbon) which is deposited on the catalyst. These known processes are employed to crack heavy paraffinic molecules into lighter molecules. However, when it is desired to produce propylene, not only are the yields low but also the stability of the crystalline silicate catalyst is low. For example, in an FCC unit a typical propylene output is 3.5 wt %. The propylene output may be increased to up to about 7–8 wt % propylene from the FCC unit by introducing the known ZSM-5 catalyst into the FCC unit to "squeeze" out more propylene from the incoming hydrocarbon feedstock being cracked. Not only is this increase in yield quite small, but also the ZSM-5 catalyst has low stability in the FCC unit.

There is an increasing demand for propylene in particular for the manufacture of polypropylene.

The petrochemical industry is presently facing a major squeeze in propylene availability as a result of the growth in propylene derivatives, especially polypropylene. Traditional methods to increase propylene production are not entirely satisfactory. For example, additional naphtha steam cracking units which produce about twice as much ethylene as propylene are an expensive way to yield propylene since the feedstock is valuable and the capital investment is very high. Naphtha is in competition as a feedstock for steam crackers because it is a base for the production of gasoline in the refinery. Propane dehydrogenation gives a high yield of propylene but the feedstock (propane) is only cost effective during limited periods of the year, making the process expensive and limiting the production of propylene. Propylene is obtained from FCC units but at a relatively low yield and increasing the yield has proven to be expensive and limited. Yet another route known as metathesis or disproportionation enables the production of propylene from ethylene and butene. Often, combined with a steam cracker, this technology is expensive since it uses ethylene as a feedstock which is at least as valuable as propylene.

EP-A-0109059 discloses a process for converting olefins having 4 to 12 carbon atoms into propylene. The olefins are contacted with an alumino-silicate having a crystalline and zeolite structure (e.g. ZSM-5 or ZSM-11) and having a $SiO_2/Al_2O_3$ molar ratio equal to or lower than 300. The specification requires high space velocities of greater than 50 kg/h per kg of pure zeolite in order to achieve high propylene yield. The specification also states that generally the higher the space velocity the lower the $SiO_2/Al_2O_3$ molar ratio (called the Z ratio). This specification only exemplifies olefin conversion processes over short periods (e.g. a few hours) and does not address the problem of ensuring that the catalyst is stable over longer periods (e.g. at least 160 hours or a few days) which are required in commercial production. Moreover, the requirement for high space velocities is undesirable for commercial implementation of the olefin conversion process.

Thus there is a need for a high yield propylene production method which can readily be integrated into a refinery or petrochemical plant, taking advantage of feedstocks that are less valuable for the market place (having few alternatives on the market).

On the other hand, crystalline silicates of the MFI type are also well known catalysts for the oligomerisation of olefins. For example, EP-A-0031675 discloses the conversion of olefin-containing mixtures to gasoline over a catalyst such as ZSM-5. As will be apparent to a person skilled in the art, the operating conditions for the oligomerisation reaction differ significantly from those used for cracking. Typically, in the oligomerisation reactor the temperature does not exceed around 400° C. and a high pressure favours the oligomerisation reactions.

GB-A-2156844 discloses a process for the isomerisation of olefins over silicalite as a catalyst. U.S. Pat. No. 4,579,989 discloses the conversion of olefins to higher molecular weight hydrocarbons over a silicalite catalyst. U.S. Pat. No. 4,746,762 discloses the upgrading of light olefins to produce hydrocarbons rich in $C_5$+ liquids over a crystalline silicate catalyst. U.S. Pat. No. 5,004,852 discloses a two-stage process for conversion of olefins to high octane gasoline wherein in the first stage olefins are oligomerised to $C_5$+ olefins. U.S. Pat. No. 5,171,331 discloses a process for the production of gasoline comprising oligomerising a $C_2$–$C_6$ olefin containing feedstock over an intermediate pore size siliceous crystalline molecular sieve catalyst such as silicalite, halogen stabilised silicalite or a zeolite. U.S. Pat. No. 4,414,423 discloses a multi-step process for preparing high-boiling hydrocarbons from normally gaseous hydrocarbons, the first step comprising feeding normally gaseous olefins over an intermediate pore size siliceous crystalline molecular sieve catalyst. U.S. Pat. No. 4,417,088 discloses the dimerising and trimerising of high carbon olefins over silicalite. U.S. Pat. No. 4,417,086 discloses an oligomerisation process for olefins over silicalite. GB-A-2106131 and GB-A-2106132 disclose the oligomerisation of olefins over catalysts such as zeolite or silicalite to produce high boiling hydrocarbons. GB-A-2106533 discloses the oligomerisation of gaseous olefins over zeolite or silicalite.

WO-A-98/56740 discloses a process for improving conversion of a hydrocarbon feedstock to light olefins in which a thermally converted hydrocarbon feedstock is contacted with a light-olefin producing cracking catalyst free of added metal oxides having hydrogenation/dehydrogenation functions.

SUMMARY OF THE INVENTION

It is an object of the present invention to provide a process for using the less valuable olefins present in refinery and petrochemical plants as a feedstock for a process which, in contrast to the prior art processes referred to above, catalytically converts olefins into lighter olefins, and in particular propylene.

It is another object of the invention to provide a process for producing propylene having a high propylene yield and purity. It is a further object of the present invention to provide such a process which can produce olefin effluents which are within, at least, a chemical grade quality.

It is yet a further object of the present invention to provide a process for producing olefins having a stable olefinic conversion and a stable product distribution over time.

It is yet a further object of the present invention to provide a process for converting olefinic feedstocks having a high yield on an olefin basis towards propylene, irrespective of the origin and composition of the olefinic feedstock.

It is a further object of the present invention to provide a process which enables the efficient desulphurisation of sulphur-containing hydrocarbon impurities from olefin feedstocks for the catalytic cracking process, which in turn reduces the demand on other sweetening or desulphurisation apparatus elsewhere in the process scheme, for example for sweetening or desulphurising other products of fractionation processes.

It is yet another object of the present invention to provide such a catalytic cracking process for olefin-containing streams whereby as a result of fractionation the fractionation products are economically useful.

The present invention provides a process for cracking an olefin-containing hydrocarbon feedstock which is selective towards light olefins in the effluent, the process comprising passing a hydrocarbon feedstock containing one or more olefins through a reactor containing a crystalline silicate selected from an MFI-type crystalline silicate having a silicon/aluminium atomic ratio of at least 180 and an MEL-type crystalline silicate having a silicon/aluminium atomic ratio of from 150 to 800 which has been subjected to a steaming step, at an inlet temperature of from 500 to 600° C., at an olefin partial pressure of from 0.1 to 2 bars and the feedstock being passed over the catalyst at an LHSV of from 5 to 30$h^{-1}$ to produce an effluent with an olefin content of lower molecular weight than that of the feedstock, wherein the olefin-containing hydrocarbon feedstock includes a $C_5$-containing overhead cut from a first fractionator which has been fed with a $C_5$+ hydrocarbon feedstock, the bottom fraction from the first fractionator being a $C_6$+ cut and the $C_5$+ hydrocarbon feedstock comprises a bottom fraction from a second fractionator which has been fed with a feedstock having at least $C_4$+ hydrocarbons, and the overhead from the second fractionator comprises a $C_4$ containing cut, optionally further containing $C_3$ hydrocarbons.

The feedstock having at least $C_4+$ hydrocarbons may be an effluent from a fluidised bed catalytic cracking (FCC) unit in an oil refinery.

The present invention further provides a process for cracking an olefin-containing hydrocarbon feedstock which is selective towards light olefins in the effluent, the process comprising passing a hydrocarbon feedstock containing one or more olefins through a reactor containing a crystalline silicate selected from an MFI-type crystalline silicate having a silicon/aluminium atomic ratio of at least 180 and an MEL-type crystalline silicate having a silicon/aluminium atomic ratio of from 150 to 800 which has been subjected to a steaming step, at an inlet temperature of from 500 to 600° C., at an olefin partial pressure of from 0.1 to 2 bars and the feedstock being passed over the catalyst at an LHSV of from 5 to $30h^{-1}$ to produce an effluent with an olefin content of lower molecular weight than that of the feedstock, feeding the effluent to a first fractionator for separating an overhead of $C_3$ and any lower hydrocarbons from a bottom fraction of $C_4+$ hydrocarbons, and feeding the bottom fraction of $C_4+$ hydrocarbons to a second fractionator for separating an overhead of $C_4$ hydrocarbons from a bottom fraction of $C_5+$ hydrocarbons.

The present invention yet further provides a process for desulphurising an olefin-containing hydrocarbon feedstock including sulphur-containing hydrocarbon compounds as impurities, the process comprising passing a hydrocarbon feedstock containing one or more olefins through a reactor containing a crystalline silicate selected from an MFI-type crystalline silicate having a silicon/aluminium atomic ratio of at least 180 and an MEL-type crystalline silicate having a silicon/aluminium atomic ratio of from 150 to 800 which has been subjected to a steaming step, at an inlet temperature of from 500 to 600° C., at an olefin partial pressure of from 0.1 to 2 bars and the feedstock being passed over the catalyst at an LHSV of from 5 to $30h^{-1}$ to produce an effluent with an olefin content of lower molecular weight than that of the feedstock and hydrogen sulphide, and removing hydrogen sulphide from the effluent.

The present invention yet further provides a process for cracking olefin-containing hydrocarbons which is selective towards light olefins, the process comprising passing first and second hydrocarbon feedstocks, both containing one or more olefins, through respective first and second reactors containing crystalline silicate to produce respectively first and second effluents which are rich in propylene, the first hydrocarbon feedstock having $C_4$ hydrocarbons as a major component and the second hydrocarbon feedstock having $C_5$ or greater hydrocarbons as a major component, separating $C_3$ and lower hydrocarbons from the first and second effluents to reduce respectively first and second bottom fractions of $C_4+$ hydrocarbons, separating $C_4$ hydrocarbons from each of the first and second bottom fractions, recycling the $C_4$ hydrocarbons separated from the second bottom fraction to the first reactor and recycling the remaining $C_5+$ hydrocarbons in the first effluent to the second reactor.

The present invention can thus provide a process wherein olefin-rich hydrocarbon streams (products) from refinery and petrochemical plants are selectively cracked not only into light olefins, but particularly into propylene. In one embodiment, the olefin-rich feedstock is passed over an MFI-type crystalline silicate catalyst with a particular Si/Al atomic ratio of either at least 180 attained after a steaming/dealumination treatment or at least 300 with the catalyst having been prepared by crystallisation using an organic template and having been unsubjected to any subsequent steaming or dealumination process. In another embodiment, the olefin-rich feedstock is passed over an MEL-type crystalline silicate catalyst, with a particular Si/Al atomic ratio and which has been steamed for example at a temperature of at least 300° C. for a period of at least 1 hour with a water partial pressure of at least 10 kPa. The feedstock may be passed over the catalyst at a temperature ranging between 500 to 600° C., an olefin partial pressure of from 0.1 to 2 bars and an LHSV of from 5 to $30h^{-1}$. This can yield at least 30 to 50% propylene based on the olefin content in the feedstock, with a selectivity to propylene for the $C_3$ species propylene and propane (i.e. a $C_3^-/C_3$ ratio) of at least 92% by weight.

In this specification, the term "silicon/aluminium atomic ratio" is intended to mean the Si/Al atomic ratio of the overall material, which may be determined by chemical analysis. In particular, for crystalline silicate materials, the stated Si/Al ratios apply not just to the Si/Al framework of the crystalline silicate but rather to the whole material.

The feedstock may be fed either undiluted or diluted with an inert gas such as nitrogen. In the latter case, the absolute pressure of the feedstock constitutes the partial pressure of the hydrocarbon feedstock in the inert gas.

BRIEF DESCRIPTION OF THE DRAWINGS

The various aspects of the present invention will now be described in greater detail however by example only with reference to the accompanying drawings, in which.

DETAILED DESCRIPTION OF THE PREFERRED EMBODIMENTS

In accordance with the present invention, cracking of olefins is performed in the sense that olefins in a hydrocarbon stream are cracked into lighter olefins and selectively into propylene. The feedstock and effluent preferably have substantially the same olefin content by weight. Typically, the olefin content of the effluent is within ±15 wt %, more preferably ±10 wt %, of the olefin content of the feedstock. The feedstock may comprise any kind of olefin-containing hydrocarbon stream. The feedstock may typically comprise from 10 to 100 wt % olefins and furthermore may be fed undiluted or diluted by a diluent, the diluent optionally including a non-olefinic hydrocarbon. In particular, the olefin-containing feedstock may be a hydrocarbon mixture containing normal and branched olefins in the carbon range $C_4$ to $C_{10}$, more preferably in the carbon range $C_4$ to $C_6$, optionally in a mixture with normal and branched paraffins and/or aromatics in the carbon range $C_4$ to $C_{10}$. Typically, the olefin-containing stream has a boiling point of from around −15 to around 180° C.

In particularly preferred embodiments of the present invention, the hydrocarbon feedstocks comprise $C_4$ mixtures from refineries and steam cracking units. Such steam cracking units crack a wide variety of feedstocks, including ethane, propane, butane, naphtha, gas oil, fuel oil, etc. Most particularly, the hydrocarbon feedstock may comprises a $C_4$ cut from a fluidized-bed catalytic cracking (FCC) unit in a crude oil refinery which is employed for converting heavy oil into gasoline and lighter products. Typically, such a $C_4$ cut from an FCC unit comprises around 50 wt % olefin. Alternatively, the hydrocarbon feedstock may comprise a $C_4$ cut from a unit within a crude oil refinery for producing methyl tert-butyl ether (MTBE) which is prepared from methanol and isobutene. Again, such a $C_4$ cut from the MTBE unit typically comprises around 50 wt % olefin. These $C_4$ cuts are fractionated at the outlet of the respective FCC or MTBE unit. The hydrocarbon feedstock may yet further comprise a $C_4$ cut from a naphtha steam-cracking unit of a petrochemical plant in which naphtha, comprising $C_5$ to $C_9$ species having a boiling point range of from about 15 to 180° C., is steam cracked to produce, inter alia, a $C_4$ cut. Such a $C_4$ cut typically comprises, by weight, 40 to 50% 1,3-butadiene, around 25% isobutylene, around 15% butene (in the form of but-1-ene and/or but-2-ene) and around 10% n-butane and/or isobutane. The olefin-containing hydrocarbon feedstock may also comprise a $C_4$ cut from a steam cracking unit after butadiene extraction (raffinate 1), or after butadiene hydrogenation.

The feedstock may yet further alternatively comprise a hydrogenated butadiene-rich $C_4$ cut, typically containing greater than 50 wt % $C_4$ as an olefin. Alternatively, the hydrocarbon feedstock could comprise a pure olefin feedstock which has been produced in a petrochemical plant.

The olefin-containing feedstock may yet further alternatively comprise light cracked naphtha (LCN) (otherwise known as light catalytic cracked spirit (LCCS)) or a $C_5$ cut from a steam cracker or light cracked naphtha, the light cracked naphtha being fractionated from the effluent of the FCC unit, discussed hereinabove, in a crude oil refinery. Both such feedstocks contain olefins. The olefin-containing feedstock may yet further alternatively comprise a medium cracked naphtha from such an FCC unit or visbroken naphtha obtained from a visbreaking unit for treating the residue of a vacuum distillation unit in a crude oil refinery.

The olefin-containing feedstock may comprise a mixture of one or more of the above-described feedstocks.

The use of a $C_5$ cut as or in the olefin-containing hydrocarbon feedstock has particular advantages because of the need to remove $C_5$ species in any event from gasolines produced by the oil refinery. This is because the presence of $C_5$ in gasoline increases the ozone potential and thus the photochemical activity of the resulting gasoline. In the case of the use of light cracked naphtha as the olefin-containing feedstock, the olefin content of the remaining gasoline fraction is reduced, thereby reducing the vapour pressure and also the photochemical activity of the gasoline.

When converting light cracked naphtha, $C_2$ to $C_4$ olefins may be produced in accordance with the process of the invention. The $C_4$ fraction is very rich in olefins, especially in isobutene, which is an interesting feed for an MTBE unit. When converting a $C_4$ cut, $C_2$ to $C_3$ olefins are produced on the one hand and $C_5$ to $C_6$ olefins containing mainly iso-olefins are produced on the other hand. The remaining $C_4$ cut is enriched in butanes, especially in isobutane which is an interesting feedstock for an alkylation unit of an oil refinery wherein an alkylate for use in gasoline is produced from a mixture of $C_3$ and $C_5$ feedstocks. The $C_5$ to $C_6$ cut containing mainly iso-olefins is an interesting feed for the production of tertiary amyl methyl ether (TAME). Surprisingly, the present inventors have found that in accordance with the process of the invention, olefinic feedstocks can be cracked selectively in the presence of an MFI-type or MEL-type catalyst so as to redistribute the olefinic content of the feedstock in the resultant effluent. The catalyst and process conditions are selected whereby the process has a particular yield on an olefin basis towards a specified olefin in the feedstocks. Typically, the catalyst and process conditions are chosen whereby the process has the same high yield on an olefin basis towards propylene irrespective of the origin of the olefinic feedstocks for example the $C_4$ cut from the FCC unit, the $C_4$ cut from the MTBE unit, the light cracked naphtha or the $C_5$ cut from the light crack naphtha, etc., This is quite unexpected on the basis of the prior art. The propylene yield on an olefin basis is typically from 30 to 50% based on the olefin content of the feedstock. The yield on an olefin basis of a particular olefin is defined as the weight of that olefin in the effluent divided by the initial total olefin content by weight. For example, for a feedstock with 50 wt % olefin, if the effluent contains 20 wt % propylene, the propylene yield on an olefin basis is 40%. This may be contrasted with the actual yield for a product which is defined as the weight amount of the product produced divided by the weight amount of the feed. The paraffins and the aromatics contained in the feedstock are only slightly converted in accordance with the preferred aspects of the invention.

In accordance with the present invention, the catalyst for the cracking of the olefins comprises a crystalline silicate of the MFI family which may be a zeolite, a silicalite or any other silicate in that family or the MEL family which may be a zeolite or any other silicate in that family. Examples of MFI silicates are ZSM-5 and silicalite. An example of an MEL zeolite is ZSM-11 which is known in the art. Other examples are Boralite D, and silicalite-2 as described by the International Zeolite Association (Atlas of zeolite structure types, 1987, Butterworths). The preferred crystalline silicates have pores or channels defined by ten oxygen rings and a high silicon/aluminium atomic ratio.

Crystalline silicates are microporous crystalline inorganic polymers based on a framework of $XO_4$ tetrahedra linked to each other by sharing of oxygen ions, where X may be trivalent (e.g. Al,B, ...) or tetravalent (e.g. Ge, Si, ...). The crystal structure of a crystalline silicate is defined by the specific order in which a network of tetrahedral units are linked together. The size of the crystalline silicate pore openings is determined by the number of tetrahedral units, or, alternatively, oxygen atoms, required to form the pores and the nature of the cations that are present in the pores. They possess a unique combination of the following properties: high internal surface area; uniform pores with one or more discrete sizes; ion exchangeability; good thermal stability; and ability to adsorb organic compounds. Since the pores of these crystalline silicates are similar in size to many organic molecules of practical interest, they control the ingress and egress of reactants and products, resulting in particular selectivity in catalytic reactions. Crystalline silicates with the MFI structure possess a bidirectional intersecting pore system with the following pore diameters: a straight channel along [010]: 0.53–0.56 nm and a sinusoidal channel along [100]: 0.51–0.55 nm. Crystalline silicates with the MEL structure possess a bidirectional intersecting straight pore system with straight channels along [100] having pore diameters of 0.53–0.54 nm.

The crystalline silicate catalyst has structural and chemical properties and is employed under particular reaction conditions whereby the catalytic cracking readily proceeds. Different reaction pathways can occur on the catalyst. Under the process conditions, having an inlet temperature of around 500 to 600° C., preferably from 520 to 600° C., yet more preferably 540 to 580° C., and an olefin partial pressure of from 0.1 to 2 bars, most preferably around atmospheric pressure, the shift of the double bond of an olefin in the feedstock is readily achieved, leading to double bond isomerisation. Furthermore, such isomerisation tends to reach a thermodynamic equilibrium. Propylene can be, for example, directly produced by the catalytic cracking of hexene or a heavier olefinic feedstock. Olefinic catalytic cracking may be understood to comprise a process yielding shorter molecules via bond breakage.

The catalyst preferably has a high silicon/aluminium atomic ratio, whereby the catalyst has relatively low acidity. Hydrogen transfer reactions are directly related to the strength and density of the acid sites on the catalyst, and such reactions are preferably suppressed so as to avoid the formation of coke during the olefin conversion process, and composition of the olefinic feedstock. Such high ratios reduce the acidity of the catalyst, thereby increasing the stability of the catalyst. Moreover, the use of high Si/Al atomic ratios has been found to increase the propylene selectivity of the catalyst, i.e. to reduce the amount of propane produced. This increases the purity of the resultant propylene.

In accordance with one aspect, a first type of MFI catalyst has a high silicon/aluminum atomic ratio, e.g. at least about 180, preferably greater than about 200, more preferably greater than about 300, whereby the catalyst has relatively low acidity. Hydrogen transfer reactions are directly related to the strength and density of the acid sites on the catalyst, and such reactions are preferably suppressed so as to avoid the formation of coke during the olefin conversion process, which in turn would otherwise decrease the stability of the catalyst over time. Such hydrogen transfer reactions tend to produce saturates such as paraffins, intermediate unstable dienes and cyclo-olefins, and aromatics, none of which favours cracking into light olefins. Cyclo-olefins are precursors of aromatics and coke-like molecules, especially in the presence of solid acids, i.e. an acidic solid catalyst. The acidity of the catalyst can be determined by the amount of residual ammonia on the catalyst following contact of the catalyst with ammonia which adsorbs to the acid sites on the catalyst with subsequent ammonium desorption at elevated temperature measured by differential thermogravimetric analysis. Preferably, the silicon/aluminum ratio ranges from 180 to 1000, most preferably from 300 to 500.

With such high silicon/aluminum ratio in the crystalline silicate catalyst, a stable olefin conversion can be achieved with a high propylene yield on an olefin basis of from 30 to 50% whatever the origin and composition of the olefinic feedstock. Such high ratios reduce the acidity of the catalyst, thereby increasing the stability of the catalyst.

The MFI catalyst having a high silicon/aluminum atomic ratio for use in the catalytic cracking process of the present invention may be manufactured by removing aluminum from a commercially available crystalline silicate. A typical commercially available silicalite has a silicon/aluminum atomic ratio of around 120. The commercially available MFI crystalline silicate may be modified by a steaming process which reduces the tetrahedral aluminum in the crystalline silicate framework and converts the aluminum atoms into octahedral aluminum in the form of amorphous alumina. Although in the steaming step aluminum atoms are chemically removed from the crystalline silicate framework structure to form alumina particles, those particles cause partial obstruction of the pores or channels in the framework.

This inhibits the olefinic cracking processes of the present invention. Accordingly, following the steaming step, the crystalline silicate is subjected to an extraction step wherein amorphous alumina is removed from the pores and the micropore volume is, at least partially, recovered. The physical removal, by a leaching step, of the amorphous alumina from the pores by the formation of a water-soluble aluminum complex yields the overall effect of dealumination of the MFI crystalline silicate.

In this way by removing aluminum from the MFI crystalline silicate framework and then removing alumina formed therefrom from the pores, the process aims at achieving a substantially homogeneous dealumination throughout the whole pore surfaces of the catalyst. This reduces the acidity of the catalyst, and thereby reduces the occurrence of hydrogen transfer reactions in the cracking process. The reduction of acidity ideally occurs substantially homogeneously throughout the pores defined in the crystalline silicate framework. This is because in the olefin cracking process hydrocarbon species can enter deeply into the prose. Accordingly, the reduction of acidity and thus the reduction in hydrogen transfer reactions which would reduce the stability of the MFI catalyst are pursued throughout the whole pore structure in the framework. The framework silicon/aluminum ratio may be increased by this process to a value of at least about 180, preferably from about 180 to 1000, more preferably at least 200, yet more preferably at least 300, and most preferably around 480.

In accordance with another aspect, a second type of MFI catalyst has a high silicon/aluminium atomic ratio, greater than about 300, whereby the catalyst has relatively low acidity and the catalyst has not been steamed or dealuminated as described hereinabove.

In accordance with a further aspect, an MEL catalyst for use in the catalytic cracking process may be manufactured by steaming an as-synthesised or commercially available crystalline silicate. The MEL crystalline silicate catalyst for use in the invention most typically comprises a ZSM-11 catalyst which may be synthesised either using diaminooctane as the templating agent and sodium silicate as the silicon source or tetrabutyl phosphonium bromide as the templating agent and a silica sol as the silicon source. Thus the ZSM-11 catalyst may be prepared by mixing sodium silicate with 1,8 diaminooctane together with aluminium sulphate to form a hydrogel which is then allowed to crystallise to form the crystalline silicate. The organic template material is then removed by calcining. Alternatively, the ZSM-11 catalyst is produced by reacting tetrabutyl phosphonium bromide and sodium hydroxide together with the silica sol prepared from colloidal silica. Again, a crystallisation is performed to produce the crystalline silicate and then the product is calcined.

In order to reduce the sodium content of the MEL crystalline silicate, the crystalline silicate is subjected to an ion exchange with a salt. Thereafter the material is dried. Typically, the crystalline silicate is subjected to ion exchange with ammonium ions, for example by immersing the crystalline silicate in an aqueous solution of $NH_4Cl$ or $NH_4NO_3$. Such an ion exchange step is desirable if the amount of sodium ions present in the crystalline silicate is so high that a crystalline sodium silicate phase is formed following calcination of the crystalline silicate which would be difficult to remove.

The initial MEL crystalline silicate may be modified by a steaming process which, without being bound by theory, is believed to reduce the tetrahedral aluminium in the crystalline silicate framework and to convert the aluminium atoms into octahedral aluminium in the form of amorphous alumina. Although in the steaming step aluminium atoms are chemically removed from the MEL crystalline silicate framework structure to form alumina particles, those particles appear not to migrate and so do not cause partial obstruction of the pores or channels in the framework which would otherwise inhibit the olefinic cracking processes of the present invention. The steaming step has been found to improve significantly the propylene yield, propylene selectivity and catalyst stability in the olefinic catalytic cracking process.

The steam treatment on the MEL catalyst is conducted at elevated temperature, preferably in the range of from 425 to 870° C., more preferably in the range of from 540 to 815° C. and at atmospheric pressure and at a water partial pressure of from 13 to 200 kPa. Preferably, the steam treatment is conducted in an atmosphere comprising from 5 to 100% steam. The steam treatment is preferably carried out for a period of from 1 to 200 hours, more preferably from 20 hours to 100 hours. As stated above, the steam treatment tends to reduce the amount of tetrahedral aluminium in the crystalline silicate framework, by forming alumina.

Following the steaming step, the MEL catalyst is thereafter calcined, for example at a temperature of from 400 to 800° C. at atmospheric pressure for a period of from 1 to 10 hours.

Following the steaming step, the MEL catalyst may be contacted by a complexing agent for aluminium which may comprise an organic acid in an aqueous solution thereof or a salt of such an organic acid or a mixture of two or more such acids or salts. The complexing agent may in particular comprise an amine, such as ethyl diamine tetraacetic acid (EDTA) or a salt thereof, in particular the sodium salt thereof. Following the contacting of the MEL crystalline silicate by the complexing agent, the crystalline silicate may be subjected to a second ion exchange step for reducing the sodium content of the crystalline silicate still further, for example by contacting the catalyst with an ammonium nitrate solution.

The MEL or MFI crystalline silicate catalyst may be mixed with a binder, preferably an inorganic binder, and shaped to a desired shape, e.g. extruded pellets. The binder is selected so as to be resistant to the temperature and other conditions employed in the catalyst manufacturing process and in the subsequent catalytic cracking process for the olefins. The binder is an inorganic material selected from clays, silica, metal oxides such as $ZrO_2$ and/or metals, or gels including mixtures of silica and metal oxides. The binder is preferably alumina-free. If the binder which is used in conjunction with the crystalline silicate is itself catalytically active, this may alter the conversion and/or the selectivity of the catalyst. Inactive materials for the binder may suitably serve as diluents to control the amount of conversion so that products can be obtained economically and orderly without employing other means for controlling the reaction rate. It is desirable to provide a catalyst having a good crush strength. This is because in commercial use, it is desirable to prevent the catalyst from breaking down into powder-like materials. Such clay or oxide binders have been employed normally only for the purpose of improving the crush strength of the catalyst. A particularly preferred binder for the catalyst of the present invention comprises silica.

The relative proportions of the finely divided crystalline silicate material and the inorganic oxide matrix of the binder can vary widely. Typically, the binder content ranges from 5 to 95% by weight, more typically from 20 to 50% by weight, based on the weight of the composite catalyst. Such a mixture of crystalline silicate and an inorganic oxide binder is referred to as a formulated crystalline silicate.

In mixing the catalyst with a binder, the catalyst may be formulated into pellets, extruded into other shapes, or formed into a spray-dried powder.

Typically, the binder and the crystalline silicate catalyst are mixed together by an extrusion process. In such a process, the binder, for example silica, in the form of a gel is mixed with the crystalline silicate catalyst material and the resultant mixture is extruded into the desired shape, for example pellets. Thereafter, the formulated crystalline silicate is calcined in air or an inert gas, typically at a temperature of from 200 to 900° C. for a period of from 1 to 48 hours.

The binder preferably does not contain any aluminium compounds, such as alumina. This is because as mentioned above the preferred catalyst has a selected silicon/aluminium ratio of the crystalline silicate. The presence of alumina in the binder yields other excess alumina if the binding step is performed prior to the aluminium extraction step. If the aluminium-containing binder is mixed with the crystalline silicate catalyst following aluminium extraction, this re-aluminates the catalyst. The presence of aluminium in the binder would tend to reduce the olefin selectivity of the catalyst, and to reduce the stability of the catalyst over time.

In addition, the mixing of the catalyst with the binder may be carried out either before or after any steaming step.

The various preferred catalysts have been found to exhibit high stability, in particular being capable of giving a stable propylene yield over several days, e.g. up to ten days. This enables the olefin cracking process to be performed continuously in two parallel "swing" reactors wherein when one reactor is operating, the other reactor is undergoing catalyst regeneration. The catalyst also can be regenerated several times. The catalyst is also flexible in that it can be employed to crack a variety of feedstocks, either pure or mixtures, coming from different sources in the oil refinery or petrochemical plant and having different compositions.

In the process for catalytic cracking of olefins when dienes are present in the olefin-containing feedstock, this can provoke a faster deactivation of the catalyst. This can greatly decrease the yield on an olefin basis of the catalyst to produce the desired olefin, for example propylene, with increasing time on stream. When dienes are present in the feedstock which is catalytically cracked, this can yield a gum derived from the diene being formed on the catalyst which in turn decreases the catalyst activity. It is desired for the catalyst to have a stable activity over time, typically for at least ten days.

In accordance with this aspect, prior to the catalytic cracking of the olefins, if the olefin-containing feedstock contains dienes, the feedstock is subjected to a selective hydrogenation process in order to remove the dienes. The hydrogenation process requires to be controlled in order to avoid the saturation of the mono-olefins. The hydrogenation process preferably comprises nickel-based or palladium-based catalysts or other catalysts which are typically used for first stage pyrolysis gasoline (Pygas) hydrogenation. When such nickel-based catalysts are used with a $C_4$ cut, a significant conversion of the mono-olefins into paraffins by hydrogenation cannot be avoided. Accordingly, such palladium-based catalysts, which are more selective to diene hydrogenation, are more suitable for use with the $C_4$ cut.

A particularly preferred catalyst is a palladium-based catalyst, supported on, for example, alumina and containing 0.2–0.8 wt % palladium based on the weight of the catalyst. The hydrogenation process is preferably carried out at an absolute pressure of from 5 to 50 bar, more-preferably from 10 to 30 bar and at an inlet temperature of from 40 to 200° C. Typically, the hydrogen/diene weight ratio is at least 1, more preferably from 1 to 5, most preferably around 3. Preferably, the liquid hourly space velocity (LHSV) is at least $2h^{-1}$, more preferably from 2 to $5h^{-1}$.

The dienes in the feedstock are preferably removed so as to provide a maximum diene content in the feedstock of around 0.1% by weight, preferably around 0.05% by weight, more preferably around 0.03% by weight.

In the catalytic cracking process, the process conditions are selected in order to provide high selectivity towards propylene, a stable olefin conversion over time, and a stable olefinic product distribution in the effluent. Such objectives are favoured by the use of a low acid density in the catalyst (i.e. a high Si/Al atomic ratio) in conjunction with a low pressure, a high inlet temperature and a short contact time, all of which process parameters are interrelated and provide an overall cumulative effect (e.g. a higher pressure may be offset or compensated by a yet higher inlet temperature). The process conditions are selected to disfavour hydrogen transfer reactions leading to the formation of paraffins, aromatics and coke precursors. The process operating conditions thus employ a high space velocity, a low pressure and a high reaction temperature. The LHSV ranges from 5 to $30h^{-1}$, preferably from 10 to $30h^{-1}$. The olefin partial pressure ranges from 0.1 to 2 bars, preferably from 0.5 to 1.5 bars. A particularly preferred olefin partial pressure is atmospheric pressure (i.e. 1 bar). The hydrocarbon feedstocks are preferably fed at a total inlet pressure sufficient to convey the feedstocks through the reactor. The hydrocarbon feedstocks may be fed undiluted or diluted in an inert gas, e.g. nitrogen. Preferably, the total absolute pressure in the reactor ranges from 0.5 to 10 bars. The use of a low olefin partial pressure, for example atmospheric pressure, tends to lower the incidence of hydrogen transfer reactions in the cracking process, which in turn reduces the potential for coke formation which tends to reduce catalyst stability. The cracking of the olefins is preferably performed at an inlet temperature of the feedstock of from 500 to 600° C., more preferably from 520 to 600° C., yet more preferably from 540 to 580° C., typically around 560° C. to 570° C.

The catalytic cracking process can be performed in a fixed bed reactor, a moving bed reactor or a fluidized bed reactor. A typical fluid bed reactor is one of the FCC type used for fluidized-bed catalytic cracking in the oil refinery. A typical moving bed reactor is of the continuous catalytic reforming type. As described above, the process may be performed continuously using a pair of parallel "swing" reactors.

Since the catalyst exhibits high stability to olefinic conversion for an extended period, typically at least around ten days, the frequency of regeneration of the catalyst is low. More particularly, the catalyst may accordingly have a lifetime which exceeds one year.

After the catalytic cracking process, the reactor effluent is sent to a fractionator and the desired olefins are separated from the effluent. When the catalytic cracking process is employed to produce propylene, the $C_3$ cut, containing at least 92% propylene, is fractionated and thereafter purified in order to remove all the contaminants such as sulphur species, arsine, etc . . . The heavier olefins of greater than $C_3$ can be recycled.

For example, olefin-rich streams from refinery or petrochemical plants are cracked into light olefins, in particular propylene. The light fractions of the effluent, namely the $C_2$ and $C_3$ cuts, can contain more than 92% olefins. Such cuts are sufficiently pure to constitute chemical grade olefin feedstocks. The propylene yield on an olefin basis in such a process can range from 30 to 50% based on the olefinic content of the feedstock which contains one or more olefins of $C_4$ or greater. In the process, the effluent has a different olefin distribution as compared to that of the feedstock, but substantially the same total olefin content.

Figure 1:
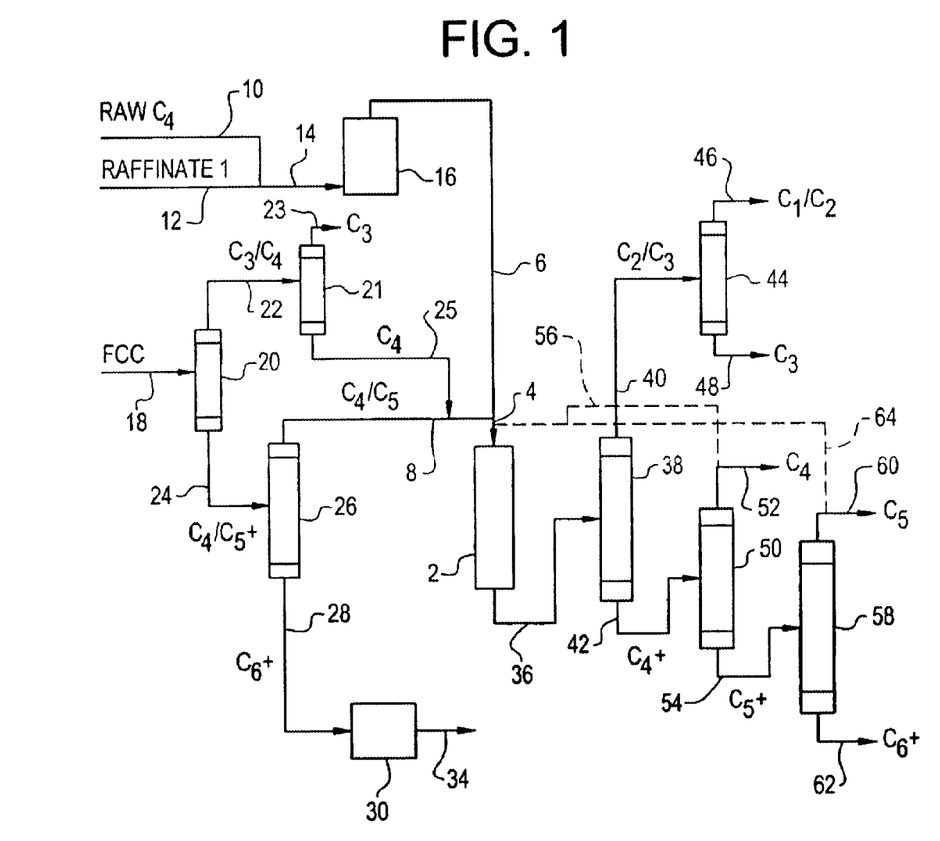
FIG. 1 shows a process scheme in accordance with one embodiment of the present invention for processing refinery and/or petrochemical feedstocks, the process scheme incorporating a process for selectively catalytically cracking olefins into lighter olefins over a crystalline silicate catalyst.

Referring to FIG. 1, there is shown a process scheme incorporating a reactor for cracking an olefin-rich hydrocarbon feedstock which is selective towards light olefins in the effluent. The process scheme integrates such a reactor into an oil refinery, which is also provided with inputs for petrochemical feedstocks.

As shown in FIG. 1, the process scheme includes a reactor 2 for selectively catalytically cracking an olefin-rich hydrocarbon feedstock to form light olefins, such as propylene. The reactor 2 is typically a fixed bed reactor, and contains as a catalyst a crystalline silicate of the MFI or MEL type as described hereinabove. The reactor 2 is also operated under the temperature, flow rate and pressure conditions as described herein for the selective catalytic cracking process. The reactor 2 is fed along an input 4 with one or more of a variety of olefin-rich hydrocarbon feedstocks. The input 4 may be supplied by a first line 6 with feedstocks derived from a petrochemical plant and/or by a line 8 with feedstocks derived from an oil refinery.

The petrochemical feedstocks which are fed along line 6 may comprise raw $C_4$ feedstocks, including $C_4$ olefins, fed along a line 10 and/or a raffinate 1 feedstock fed along a line 12 which comprises a $C_4$ cut from a steam cracking unit after butadiene extraction. Both of those feedstocks are sent, prior to line 6, via a common input 14 to a selective hydrogenation reactor 16 in which the feedstock is selectively hydrogenated, for example over a nickel-based or palladium-based catalyst as described hereinabove, for removing dienes from the feedstock which otherwise would reduce the stability of the catalyst in the reactor 2.

Line 8 is fed with a $C_4/C_5$ olefin-containing feedstock which in this embodiment has been derived from a fluidised-bed catalytic cracking (FCC) unit in a crude oil refinery which is employed for converting heavy oil into gasoline and lighter products. The feedstock on line 8 typically comprises up to about 50 wt % olefin.

A feedstock having at least $C_4$+ hydrocarbons, in this embodiment comprising effluent from the FCC, is fed into a line 18 communicating with the FCC unit in the oil refinery and to a debutaniser 20 which, in a known manner, fractionates the feedstocks into $C_4$ and lower hydrocarbons which are outputted as an overhead along a line 22 at the top of the debutaniser 20 and $C_5$+ species which are outputted along a line 24 at the bottom of the debutaniser 20. The feedstock on line 18 may include $C_1$ to $C_3$ hydrocarbons as well as $C_4$+ hydrocarbons. The feedstock on line 18 may alternatively comprise effluents containing visbroken naptha, coker naptha and pyrolysis gasoline. The hydrocarbon fraction along line 22 includes propylene and $C_4$ species and thus may be fed to a liquid petroleum gas (LPG) recovery system. The $C_3$ and $C_4$ on line 22 may be separated by a depropaniser 21 of the recovery system with a $C_3$ overhead output on line 23, and a $C_4$ recycle bottom fraction on line 25 which communicates with line 8. Alternatively, the $C_4$ bottom fraction on line 25 could be sent to an alkylation unit.

The debutaniser 20 is operated in a mode whereby some of the $C_4$ content of the feedstock is outputted in the bottom fraction along line 24 thereby to reduce the proportion of $C_4$ content in the overhead along line 22 to form the LPG pool.

This enhances the propylene proportion in the LPG pool and unloads the downstream recovery system.

Downstream of the line 24 is provided a depentaniser 26 which fractionates the incoming $C_4/C_5+$ feedstock on line 24 into an overhead $C_4/C_5$ fraction which is fed along line 8 for input into the reactor 2 and into a bottom $C_6+$ fraction which is fed along a line 28. The provision of the depentaniser 26 downstream of the debutaniser 20, with the depentaniser 26 additionally separating, in the overhead for feeding to the reactor 2, $C_4$ hydrocarbons which are then fed to the reactor 2, permits the debutaniser to be operated in what is known as "winter mode" whereby $C_4$ hydrocarbons can be outputted from the bottom of the debutaniser 20 thereby reducing the $C_4$ content of the LPG pool feed on line 22.

The $C_6+$ feedstock on line 28 is fed to a sweetening unit 30, such as a Merox unit, in which mercaptans in the hydrocarbons are converted into disulphides. The effluent along line 34 comprises a $C_6+$ sweetened cut which is fed to a gasoline blending system. The $C_6+$ cut has a low content of light olefins which is particularly desirable because such light olefins are not desirable in gasoline as these tend to increase the residual vapour pressure of the gasoline, which is environmentally unacceptable.

The provision the depentaniser 26 provides the advantage that heavy $C_6+$ olefins and aromatics are removed from the feed for the reactor 2, which otherwise would reduce the run length of the catalyst in the reactor 2 in order to be able to crack selectively the olefin-containing feedstock.

The selective catalytic cracking process in the reactor 2, as well as cracking the feedstock olefins into lighter olefins, in particular propylene, also desulphurises the incoming hydrocarbon feedstock by decomposition (or cracking) of mercaptans (which may be present as impurities) into valuable olefins and hydrogen sulphide. The hydrogen sulphide is subsequently removed in the reactor 2 or from the effluent by techniques known in the art. The use of an MFI-type crystalline silicate such as silicalite which is not highly sensitive to poisoning by heteroatoms such as sulphur in combination with this desulphurisation process enables the provision of a smaller sweetening unit 30, or the provision of a sweetening unit 30 operating under reduced load, than would otherwise be required for treating an FCC feedstock containing sulphur as an impurity, such as that fed along line 18. Thus the use of the reactor 2 for selective catalytic cracking of the olefin-containing hydrocarbon feedstock additionally desulphurises the incoming $C_4+$ FCC effluent thereby reducing the capital and operating costs of the known sweetening unit 30 for FCC effluents.

The effluent from the reactor 2 is outputted along a line 36 to a depropaniser 38. In the depropaniser 38, the effluent fed along line 36 is fractionated into a $C_2/C_3$ overhead fraction outputted along line 40 and a $C_4+$ bottom fraction outputted along line 42. The $C_2/C_3$ fraction, including a high proportion of propylene, is fed to a fractionator 44 at which an overhead $C_2$ fraction outputted along line 46 is separated from a bottom $C_3$ fraction outputted along line 48. The $C_3$ fraction has a high proportion, typically greater than 92 wt %, propylene. This comprises chemical-grade propylene which may be used in subsequent processes as a starting feedstock, for example in the production of polypropylene.

The $C_4+$ feedstock outputted on line 42 from the depropaniser 38 is fed to a debutaniser 50 which separates the incoming effluent into an overhead $C_4$ fraction outputted on line 52 and a bottom $C_5+$ fraction outputted on line 54. The $C_4$ fraction on line 52 includes a reduced proportion of $C_4$ olefins as a result of the catalytic cracking in reactor 2 of the $C_4$ olefins into propylene. The effluent on line 52 may be recycled to the reactor 2, as shown by the dashed line 56 in FIG. 1, in order further to deplete the olefin content of the $C_4$ purge on line 52. Alternatively, the $C_4$ purge on line 52 may be fed to an alkylation unit as a subsidiary alkylation feed; to a steam cracker; to a unit for producing, together with methanol, methyltert-butyl ether (MTBE) when the effluent is rich in isobutene; and/or to a gasoline pool or blending system if the $C_4$ effluent has low olefin content.

The $C_5+$ effluent on line 54 is fed to a depentaniser 58 in which the effluent is fractionated to yield an overhead Cs fraction 30 which is outputted on line 60 and a bottom $C_6+$ fraction which is outputted on line 62. The overhead $C_5$ fraction may be recycled to the reactor 2 as represented by the dashed line 64; fed to the gasoline pool; fed to an alkylation unit; or if rich in isopentene, fed to a unit for producing tertiary amyl methyl ether (TAME). The $C_6+$ cut on line 62 is rich in aromatics and may be sent to a unit for processing such aromatics, such as a Pygas extraction unit.

The provision, downstream of the reactor 2, of a cascade of fractionators comprising the depropaniser 38, the debutaniser 50 and the depentaniser 58 enables the separation from the effluent on line 36 of streams reduced in olefin content relative to the incoming feedstocks on lines 10 and 18, to form useful feedstocks for other processes, so that for example the $C_4$ purge on line 52 and/or the $C_5$ purge on line 60 can be fed to a gasoline pool as they have low olefin content. The provision of the depentaniser 58 additionally separates the incoming $C_5+$ stream along line 54 into $C_5$ and $C_6+$ fractions, the $C_6+$ fraction having a high aromatics content, the $C_5+$ stream otherwise not being able to be sent directly to the gasoline pool due to its high aromatics content.

The provision, upstream of the reactor 2, of a cascade of fractionators comprising the debutaniser 20 and the depentaniser 26 enables the incoming refinery feedstock on line 18, in the illustrated embodiment the FCC effluent, to be successively fractionated to enable propylene and other $C_3$ species to be separated from the feedstock for transmission to an LPG pool with relatively low $C_4$ content and for a $C_4$ and $C_5$ containing fraction as an overhead from the depentaniser 26 to be fed to the reactor 2 having been separated from the $C_6+$ bottom fraction which is then treated to sweeten that fraction. The provision of the depentaniser 26 downstream of the debutaniser 20 provides the advantage that the debutaniser 20 can be operated "in winter mode" thereby reducing the $C_4$ content of the overhead from the debutaniser 20 with the excess $C_4$ being separated by the depentaniser 26 and fed into the fixed bed reactor 2. In this way, the incoming FCC effluent on line 18 can be readily separated into useful products with minimum recycling.

The present invention in providing a process scheme which integrates the selective cracking of olefin-containing hydrocarbon feedstocks to produce propylene, provides commercially attractive treatments for raw $C_4$ and raffinate 1 streams coming from a petrochemical plant which otherwise would need to be processed in other reaction schemes which may occur additional capital costs and running costs. For example, absent the process scheme of the invention, the raw $C_4$ petrochemical streams could be recycled back to a steam cracking unit, for example to make ethylene and propylene, but this would significantly decrease the run length of the furnaces of the steam cracker. Alternatively, the raw $C_4$ streams could be sent to an alkylation unit, but this would require preliminary hydrogenation of the raw $C_4$ feed, requiring high volumes of hydrogen gas, thereby increasing the operating cost. Alternatively, the raw $C_4$ streams could be subjected to catalytic polymerisation, for example to produce high octane streams, again requiring a high volume of hydrogen.

Figure 2:
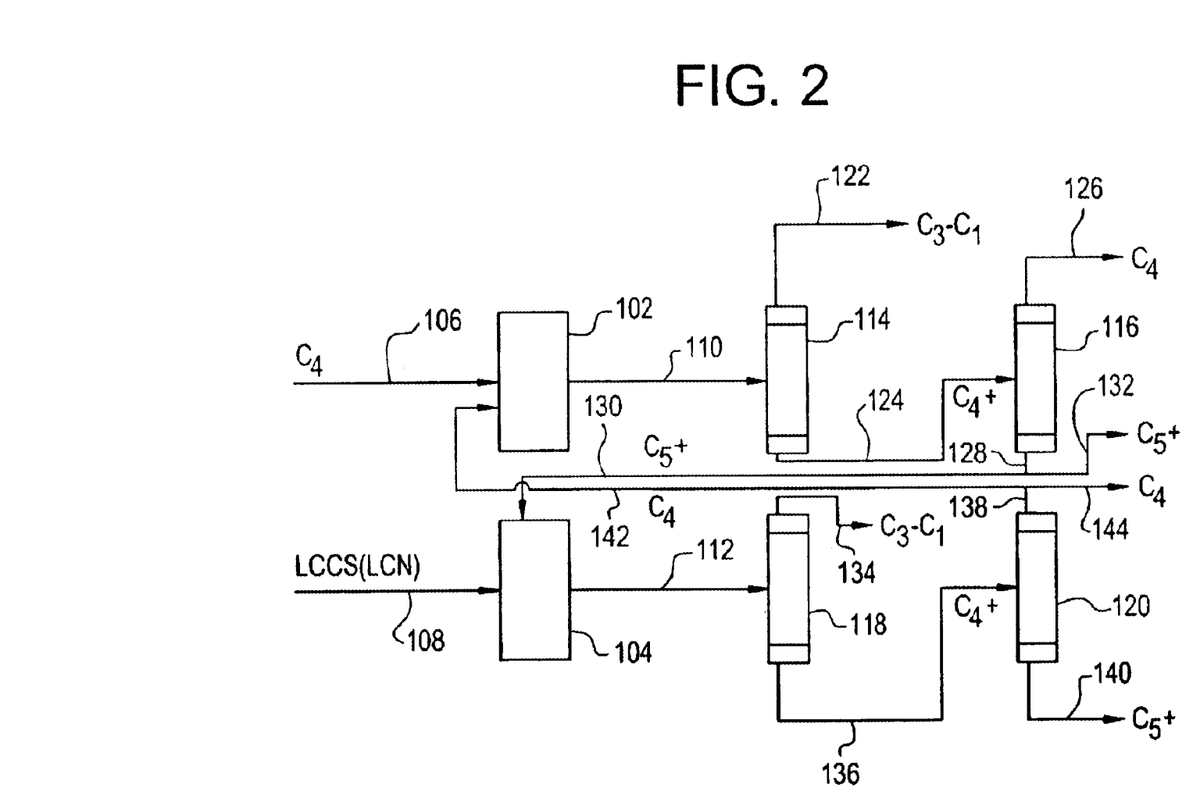
FIG. 2 shows such a process scheme in accordance with a second embodiment of the present invention.

A further embodiment of a process for cracking an olefin-rich hydrocarbon feedstock which is selective towards light olefins in the feedstock is illustrated by the process scheme of FIG. 2.

In this embodiment, two fixed bed reactors 102, 104 are disposed in parallel for respectively receiving an olefin-containing feedstock rich in $C_4$ (such as described hereinabove) along line 106 and an olefin-containing feedstock rich in $C_5$ along line 108. The latter feedstock in the illustrated embodiment comprises a LCCS (otherwise known as LCN), but in alternative arrangements other different feedstocks may be employed such as a $C_5$ cut from LCCS, a visbroken naptha, a coker naptha or a pyrolysis gasoline fraction. Each fixed bed reactor 102, 104 is operated, as for the reactor 2 of the embodiment of FIG. 1, to crack the olefins in the feedstock respectively fed thereto selectively to produce propylene in the effluent which is respectively outputted on lines 110, 112. Each fixed bed reactor 102, 104 is provided with a respective cascade of fractionators 114, 116, 118, 120 downstream thereof. These cascades are arranged so that one effluent hydrocarbon fraction which is fractionated from the effluent of a first fixed bed reactor 102 is fed back as a secondary feedstock of the second fixed bed reactor 104, and correspondingly another effluent hydrocarbon fraction which is fractionated from the effluent of the second fixed bed reactor 104 is fed back as a secondary feedstock of the first fixed bed reactor 102. In this way, by using a pair of parallel olefin cracking reactors 102, 104 with complementary feedstocks and effluent fractionation, recycling of portions of the effluents is employed for optimising the olefin cracking process and to yield commercially useful products in the unrecycled fractions of the effluents, particularly propylene, $C_4$ and $C_5+$ fractions. The use of two parallel olefin cracking reactors with overlapping recycle streams thus increases the efficiency and flexibility of the process of the invention.

The effluent from the first fixed bed reactor 102 is fed along line 110 to a depropaniser 114. A $C_3$–$C_1$ overhead on line 122 is separated off and propylene is subsequently recovered by downstream fractionation. The $C_4+$ bottom fraction is fed along line 124 to a debutaniser 116 in which a $C_4$ overhead is separated along line 126 from a $C_5+$ bottom fraction outputted on line 128. The $C_5+$ bottom fraction has a composition rich in olefins of $C_5$ and accordingly is quite similar to that of the LCCS feedstock fed to the second fixed bed reactor 104. In this embodiment therefore, the $C_5+$ bottom fraction is fed back to the second fixed bed reactor 104 along line 130 communicating with line 128, thereby constituting a secondary feedstock for the second fixed bed reactor 104. All or part of the $C_5$ 30 bottom fraction may alternatively, at certain times in the process, be outputted along line 132 which additionally communicates with line 128. As for the embodiment of FIG. 1, the $C_4$ fraction on line 126 may be fed to an alkylation unit, a steam cracker, an MTBE unit and/or a gasoline pool. The $C_5+$ fraction on line 132 may, as for the embodiment of FIG. 1 and specifically such a fraction on line 54, be subsequently fractionated into a $C_5$ fraction and a $C_6+$ cut.

Correspondingly, the effluent from the second fixed bed reactor 104 is fed along line 112 to a depropaniser 118 and a $C_3$–$C_1$ overhead is separated along line 134 from a $C_4+$ bottom fraction which is fed along a line 136 to a debutaniser 120. In the debutaniser 120, a $C_4$ overhead is separated on line 138 from a $C_5+$ bottom fraction outputted on line 140. The $C_5+$ bottom fraction may be subsequently processed in the same manner as the corresponding fraction on line 132. The $C_4$ fraction is fed back to the first fixed bed reactor 102 as a secondary feed along line 142 and/or outputted on line 144 for subsequent processing as for the corresponding $C_4$ cut on line 126.

The feedback streams on line 130 for the $C_5+$ fraction and on line 142 for the $C_4$ fraction may be controlled to achieve the desired mass balance and throughputs in the fixed bed reactors 102, 104 and fractionators 114, 116, 118, 120. In the fixed bed reactors 102, 104, the same catalysts and cracking conditions are employed as for the embodiment of FIG. 1, but the fixed bed reactors 102, 104 may be operated under different conditions and with different catalysts.

Accordingly, in accordance with the present invention, the use of the selective catalytic cracking of an olefin-containing hydrocarbon feedstock provides an economic solution for the processing of excess $C_4$ streams to provide useful commercial products comprising propylene and other cuts, for example $C_4$ and/or $C_5$ cuts, which, by being low in olefins, may be fed to a gasoline pool. The process scheme of the invention minimises recycling of streams, thereby optimising the economic returns since the products produced by the reactor and the fractionators are commercially useful without needing to be recycled. Currently, the raffinate 1 feedstock is a preferred feedstock for the production of MTBE. However, as a result of environmental concerns, the production of MTBE is likely to decrease over time, thereby resulting in a reduced demand for raffinate 1 as a feedstock. The process of the present invention incorporating the selected catalytic cracking of olefin-containing hydrocarbon feedstocks such as raffinate 1 constitutes an economically attractive process for converting the excess raffinate 1 feedstock into useful products, comprising propylene and for example $C_4$ and/or $C_5$ feeds for a gasoline pool.

What is claimed is:

1. A process for desulfurising an olefin-containing hydrocarbon feedstock including sulphur-containing hydrocarbon compounds as impurities, the process comprising passing a hydrocarbon feedstock containing one or more olefins through a reactor containing a crystalline silicate selected from the group consisting of an MFI-type crystalline silicate having a silicon/aluminum atomic ratio of at least 180 and an MEL-type crystalline silicate having a silicon/aluminum atomic ratio of from 150 to 800 which has been subjected to a steaming step, at an inlet temperature of from 500 to 600° C., at an olefin partial pressure of from 0.1 to 2 bars and the feedstock being passed over, the catalyst at an LHSV of from 5 to 30$h^{-1}$ to produce an effluent with an olefin content of lower molecular weight than that of the feedstock and hydrogen sulphide, and removing hydrogen sulphide from the effluent.

2. A process according to claim 1 wherein the olefin-containing hydrocarbon feedstock includes a $C_5$-containing overhead cut from a first fractionator which has been fed with a $C_5+$ hydrocarbon feedstock, the bottom fraction from the first fractionator being a $C_6+$ cut which is fed to a sweetening unit to produce a $C_6+$ sweetened effluent.

3. A process according to claim 2 wherein the $C_5+$ hydrocarbon feedstock comprises a bottom fraction from a second fractionator which has been fed with a feedstock having at least $C_4+$ hydrocarbons, and the overhead from the second fractionator comprises a $C_4$ containing cut, optionally further containing $C_3$ hydrocarbons.

4. A process according to claim 2 wherein the $C_5+$ hydrocarbon feedstock and the $C_5$-containing overhead cut from the first fractionator further include $C_4$ hydrocarbons.

5. A process according to claim 1 wherein the olefin-containing hydrocarbon feedstock includes at least one of a $C_4$ feedstock or a raffinate 1 feedstock.

6. A process according to claim 5 wherein the at least one $C_4$ feedstock and raffinate 1 feedstock has been hydrogenated thereby to reduce the diene content thereof.

7. A process according to claim 1 wherein the effluent is fed to a third fractionator for separating an overhead of $C_3$ and any lower hydrocarbons from a bottom fraction of $C_4+$ hydrocarbons.

8. A process according to claim 7 wherein the overhead of $C_3$ and any lower hydrocarbons is fed to a fourth fractionator for separating a bottom fraction of $C_3$ hydrocarbons, including propylene, from an overhead of $C_2$ to $C_1$ hydrocarbons.

9. A process according to claim 7 wherein the bottom fraction of $C_4+$ hydrocarbons is fed to a fifth fractionator for separating an overhead of $C_4$ hydrocarbons from a bottom fraction of $C_5+$ hydrocarbons.

10. A process according to claim 9 wherein at least a part of the overhead of $C_4$ hydrocarbons is recycled to the reactor.

11. A process according to claim 9 wherein the bottom fraction of $C_5+$ hydrocarbons is fed to a sixth fractionator for separating an overhead of $C_5$ hydrocarbons from a bottom fraction of $C_6+$ hydrocarbons.

12. A process according to claim 11 wherein at least a part of the overhead of $C_5$ hydrocarbons is recycled to the reactor.

* * * * *

UNITED STATES PATENT AND TRADEMARK OFFICE
CERTIFICATE OF CORRECTION

PATENT NO. : 6,858,133 B2  Page 1 of 1
DATED : February 22, 2005
INVENTOR(S) : Jean-Pierre Dath, Walter Vermeiren and Koen Herrebout It is certified that error appears in the above-identified patent and that said Letters Patent is hereby corrected as shown below:

Column 17,
Line 53, replace "$C_5 30$" with -- $C_{5+}$ --.

Signed and Sealed this

Fourth Day of April, 2006

JON W. DUDAS
*Director of the United States Patent and Trademark Office*